US010551605B2

(12) United States Patent
Arbore et al.

(10) Patent No.: US 10,551,605 B2
(45) Date of Patent: Feb. 4, 2020

(54) CONFOCAL INSPECTION SYSTEM HAVING NON-OVERLAPPING ANNULAR ILLUMINATION AND COLLECTION REGIONS

(71) Applicant: Apple Inc., Cupertino, CA (US)

(72) Inventors: Mark Alan Arbore, Los Altos, CA (US); Matthew A. Terrel, Campbell, CA (US); Edward L. Hull, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/717,573

(22) Filed: Sep. 27, 2017

(65) Prior Publication Data
US 2018/0017772 A1    Jan. 18, 2018

Related U.S. Application Data

(63) Continuation of application No. 15/529,445, filed as application No. PCT/US2015/067445 on Dec. 22, 2015, now abandoned.
(Continued)

(51) Int. Cl.
*G02B 21/08* (2006.01)
*G02B 21/00* (2006.01)
(Continued)

(52) U.S. Cl.
CPC .......... *G02B 21/0032* (2013.01); *G01N 21/49* (2013.01); *G01N 21/55* (2013.01);
(Continued)

(58) Field of Classification Search
CPC .. G02B 21/032; G02B 21/006; G02B 21/084; G01N 21/55; G01N 2201/064; G01N 2201/0668
See application file for complete search history.

(56) References Cited

U.S. PATENT DOCUMENTS 3,013,467 A    12/1961 Minsky
4,810,077 A    3/1989 Sting
(Continued)

FOREIGN PATENT DOCUMENTS

EP    0 168 983 A1    1/1986
EP    0 943 950 A1    9/1999
(Continued)

OTHER PUBLICATIONS

Non-Final Office Action dated Apr. 6, 2018, for U.S. Appl. No. 15/529,451, filed May 24, 2017, 22 pages.
(Continued)

*Primary Examiner* — Rebecca C Bryant
(74) *Attorney, Agent, or Firm* — Brownstein Hyatt Farber Schreck, LLP

(57) ABSTRACT

A confocal inspection system can optically characterize a sample. An objective lens, which can be a single lens or a combination of separate illumination and collection lenses, can have a pupil. The objective lens can deliver incident light to the sample through an annular illumination region of the pupil, and can collect scattered light returning from the sample to form collected light. Confocal optics can be positioned to receive the collected light. A detector can be configured with the confocal optics so that the detector generates signals from light received from a specified depth at or below a surface of the sample and rejects signals from light received from depths away from the specified depth. An optical element, such as a mask, a reconfigurable panel, or the detector, can define the annular collection region to be non-overlapping with the annular illumination region in the pupil.

8 Claims, 16 Drawing Sheets

Related U.S. Application Data

(60) Provisional application No. 62/096,270, filed on Dec. 23, 2014.

(51) Int. Cl.
  *G01N 21/49* (2006.01)
  *G01N 21/55* (2014.01)
  *G02B 21/10* (2006.01)
  *G02B 21/16* (2006.01)

(52) U.S. Cl.
  CPC ......... *G02B 21/006* (2013.01); *G02B 21/008* (2013.01); *G02B 21/0076* (2013.01); *G02B 21/084* (2013.01); *G01N 2201/063* (2013.01); *G02B 21/10* (2013.01); *G02B 21/16* (2013.01)

(56) References Cited

U.S. PATENT DOCUMENTS

| | | | |
|---|---|---|---|
| 4,827,125 | A | 5/1989 | Goldstein |
| 4,975,581 | A | 12/1990 | Robinson et al. |
| 5,065,008 | A | 11/1991 | Hakamata et al. |
| 5,475,235 | A | 12/1995 | Phillips et al. |
| 5,483,261 | A | 1/1996 | Yasutake |
| 5,488,204 | A | 1/1996 | Mead et al. |
| 5,825,352 | A | 10/1998 | Bisset et al. |
| 5,835,079 | A | 11/1998 | Shieh |
| 5,880,411 | A | 3/1999 | Gillespie et al. |
| 5,936,739 | A | 8/1999 | Cameron et al. |
| 5,946,100 | A | 8/1999 | Ishihara |
| 6,122,042 | A | 9/2000 | Wunderman et al. |
| 6,188,391 | B1 | 2/2001 | Seely et al. |
| 6,248,988 | B1 | 6/2001 | Krantz |
| 6,310,610 | B1 | 10/2001 | Beaton et al. |
| 6,323,846 | B1 | 11/2001 | Westerman et al. |
| 6,353,226 | B1 | 3/2002 | Khalil et al. |
| 6,424,416 | B1 | 7/2002 | Gross et al. |
| 6,519,033 | B1 | 2/2003 | Quist et al. |
| 6,587,703 | B2 | 7/2003 | Cheng et al. |
| 6,690,387 | B2 | 2/2004 | Zimmerman et al. |
| 6,794,658 | B2 | 9/2004 | MacAulay et al. |
| 7,015,894 | B2 | 3/2006 | Morohoshi |
| 7,184,064 | B2 | 2/2007 | Zimmerman et al. |
| 7,372,985 | B2 | 5/2008 | So et al. |
| 7,433,042 | B1 | 10/2008 | Cavanaugh et al. |
| 7,440,659 | B2 | 10/2008 | Liu et al. |
| 7,460,248 | B2 | 12/2008 | Kurtz et al. |
| 7,663,607 | B2 | 2/2010 | Hotelling et al. |
| 8,040,495 | B2 | 10/2011 | Hendriks et al. |
| 8,140,147 | B2 | 3/2012 | Maynard et al. |
| 8,479,122 | B2 | 7/2013 | Hotelling et al. |
| 8,547,535 | B2 | 10/2013 | Tezuka et al. |
| 8,619,237 | B2 | 12/2013 | Hillman et al. |
| 8,866,107 | B2 | 10/2014 | Cui |
| 8,958,858 | B2 | 2/2015 | Tezuka et al. |
| 9,013,684 | B2 | 4/2015 | Xalter et al. |
| 9,395,293 | B1 | 7/2016 | Acosta et al. |
| 9,442,084 | B2 | 9/2016 | Kakefuda et al. |
| 9,494,535 | B2 | 11/2016 | Sezginer et al. |
| 9,597,024 | B2 | 3/2017 | Robinson et al. |
| 10,274,426 | B2 | 4/2019 | Arbore |
| 2004/0113059 | A1 | 6/2004 | Kawano et al. |
| 2004/0212866 | A1 | 10/2004 | Endo et al. |
| 2006/0197753 | A1 | 9/2006 | Hotelling |
| 2007/0057211 | A1 | 3/2007 | Bahlman et al. |
| 2008/0124070 | A1* | 5/2008 | Liang ............... G03B 9/04 396/435 |
| 2009/0284835 | A1* | 11/2009 | Meshulach ........ G02B 21/0068 359/486.01 |
| 2009/0310132 | A1 | 12/2009 | Bennett et al. |
| 2011/0184260 | A1 | 7/2011 | Robinson et al. |
| 2012/0070817 | A1 | 3/2012 | Wang et al. |
| 2012/0147377 | A1 | 6/2012 | Schleipen et al. |
| 2012/0281258 | A1 | 11/2012 | Sheblee et al. |
| 2014/0043620 | A1 | 2/2014 | Ishii et al. |
| 2014/0192355 | A1 | 7/2014 | Froigneux et al. |
| 2016/0091368 | A1 | 3/2016 | Fish et al. |
| 2018/0017491 | A1 | 1/2018 | Arbore |
| 2018/0039055 | A1 | 2/2018 | Arbore |
| 2019/0128734 | A1 | 5/2019 | Arbore |

FOREIGN PATENT DOCUMENTS

| | | |
|---|---|---|
| JP | 2000-163031 A | 6/2000 |
| JP | 2002-342033 A | 11/2002 |
| KR | 10-2009-0116731 A | 11/2009 |
| WO | WO-2006/086566 A2 | 8/2006 |
| WO | WO-2016/106368 A1 | 6/2016 |
| WO | WO-2016/109355 A1 | 7/2016 |
| WO | WO-2017/184420 A1 | 10/2017 |

OTHER PUBLICATIONS

Non-Final Office Action dated May 15, 2018, for U.S. Appl. No. 15/717,651, filed Sep. 27, 2017, 15 pages.

Final Office Action dated Nov. 30, 2018, for U.S. Appl. No. 15/529,451, filed May 24, 2017, 19 pages.

Aguirre, A. D. et al. (Feb. 17, 2010). "High speed optical coherence microscopy with autofocus adjustment and a miniaturized endoscopic imaging probe," Optical Society of America, vol. 18, No. 5, Retrieved from the Internet: URL:http://www.ncbi.nlm.nih.gov/pmc/articles/PMC2908909/pdl/oe-18-5-4222.pdf, retrieved on Oct. 31, 2014, figures 1, 7, p. 4226-4235.

International Search Report dated Apr. 5, 2016, for PCT Application No. PCT/US2015/067480, filed Dec. 22, 2015, four pages.

International Search Report dated Apr. 25, 2016, for PCT Application No. PCT/US2015/067463, filed Dec. 22, 2015, five pages.

Ke, S. et al. (Feb. 10, 2009) "Three-dimensional coherent transfer function for a confocal microscope with two D-shaped pupils," Applied Optics, Optical Society of America, Washington, DC; US, vol. 48, No. 5, pp. 810-817.

Kurugol, S. et al. (2011). "Semi-automated Algorithm for Localization of Dermal/Epidermal Junction in Reflectance Confocal Microscopy Images of Human Skin," Proc. of SPIE, vol. 7904, ten pages.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

Non-Final Office Action dated May 1, 2019, for U.S. Appl. No. 15/529,451, filed May 24, 2017, 20 pages.

Notice of Allowance dated Dec. 14, 2018, for U.S. Appl. No. 15/717,651, filed Sep. 27, 2017, 8 pages.

* cited by examiner

CONFOCAL INSPECTION SYSTEM HAVING NON-OVERLAPPING ANNULAR ILLUMINATION AND COLLECTION REGIONS

CROSS-REFERENCE TO RELATED APPLICATIONS

This application is a continuation of U.S. application Ser. No. 15/529,445, filed on May 24, 2017, which is a National Phase Patent Application under 35 U.S.C. § 371 of International Application No. PCT/US2015/067445, filed Dec. 22, 2015, which claims the benefit of U.S. Provisional Application No. 62/096,270 filed on Dec. 23, 2014, which are hereby incorporated by reference in their entirety.

TECHNICAL FIELD

The present disclosure relates to a confocal inspection system that uses annular illumination and annular collection.

BACKGROUND

Many optical inspection systems deliver light to a sample, collect light reflected or scattered from the sample, and use the collected light to analyze a portion of the sample. It can be desirable to improve these optical inspection systems.

SUMMARY OF THE DISCLOSURE

A confocal inspection system can optically characterize a sample. An objective lens, which can be a single lens or a combination of separate illumination and collection lenses, can have a pupil. The objective lens can deliver incident light to the sample through an annular illumination region of the pupil, and can collect scattered light returning from the sample to form collected light. Confocal optics can be positioned to receive the collected light. A detector can be configured with the confocal optics so that the detector generates signals from light received from a specified depth at or below a surface of the sample and rejects signals from light received from depths away from the specified depth. An optical element, such as a mask, a reconfigurable panel, or the detector, can define the annular collection region to be non-overlapping with the annular illumination region in the pupil. In various embodiments, the annular collection region is defined by a computer using software.

Annular illumination and annular collection can ensure that the optical path length traversed within the sample is nearly the same for all collected rays, which can be advantageous for absorptive or scattering samples. The annular illumination region and the annular collection region can be non-overlapping in the pupil, which can exclude light retroreflected by the sample.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1:
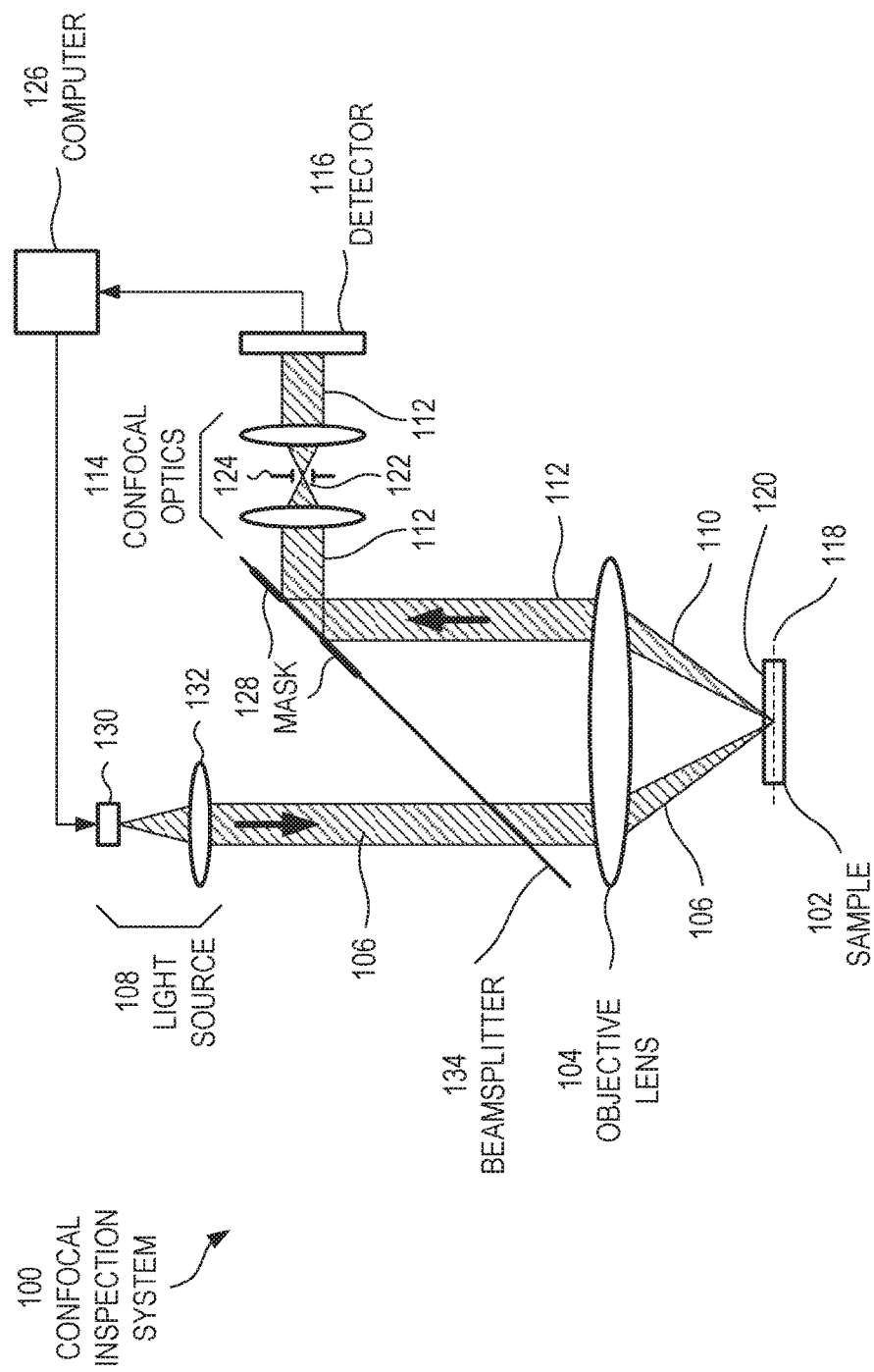
FIG. 1 is a schematic side view of an example of a confocal inspection system, in which the annular collection region is defined by a mask positioned between the objective lens and the confocal optics, in accordance with some embodiments.

FIG. 1 is a schematic side view of an example of a confocal inspection system 100 for optically characterizing a sample 102, in accordance with some embodiments. The sample 102 is not part of the confocal inspection system 100, as the other samples discussed below are not part of their corresponding confocal inspection systems. The configuration of FIG. 1 is one example of a confocal inspection system; other configurations can also be used without departing from the present subject matter.

The confocal inspection system 100 includes an objective lens 104 having a pupil. In some examples, the objective lens 104 can include a single lens or mirror, having a single pupil. In some examples, the objective lens 104 includes multiple cascaded lens elements and/or mirrors, all having a single pupil. In some examples, the objective lens 104 includes separate illumination elements and collection elements (see FIG. 6), with separate pupils for illumination and collection. For the purposes of this document, the separate illumination and collection pupils can be treated as a single pupil. Configurations using separate illumination and collection elements are discussed below with reference to FIG. 15.

The objective lens 104 has a pupil, which is shown in end-on views below in FIGS. 8-14. In some examples, the pupil is a physical structure, such as a screen with a hole therethrough, the hole defining the pupil. In other examples, the pupil is not a physical structure, but is a virtual image of an aperture stop, where the aperture stop is a physical structure within the objective lens 104. In most examples, the pupil is circular, and is arranged in a plane parallel to a top surface of the sample 102. In some examples, an incident optical path includes one or more additional imaging elements, such as relay lenses, which can image a mask or another suitable plane onto a pupil of the objective lens 104. For simplicity, the Figures are drawn under the assumption that light bends at a single plane at the objective lens, even though in practice, light can bend at more than one plane within the objective lens.

The light source 108 can produce incident light 106. The light sources of the systems described herein, such as light source 108, can include one or more light-producing elements 130. Examples of suitable light-producing elements 130 include, but are not limited to: a semiconductor laser, a light emitting diode, a quantum cascade laser, a superluminescent light source, and an amplified spontaneous emission source. The light source 108 can include a number of combinations of one or more of the suitable light-producing elements 130. In some examples, one or more of the light-producing elements 130 can be tunable. In some examples, two or more of the light-producing elements 130 can emit light at different wavelengths. In some examples, the light source 108 can include one or more collimating or focusing elements 132, which can collimate or focus light produced by the one or more light-producing elements 130. In some examples, the one or more collimating or focusing elements 132 can be made integral with the light-producing elements 130. In other examples, the one or more collimating or focusing elements 132 can be made separately and attached to the light-producing elements 130. In some examples, the light source 108 can be controlled by a computer, such as 126.

In some examples, the light-producing elements can be modulated independently and simultaneously at unique assigned frequencies. Modulation of the light source can include switching each light-producing element on and off periodically (e.g., digital modulation), or periodically varying the output intensity of each light-producing element (e.g., analog modulation), such as between zero and a peak value or between a relatively low value and a relatively high value.

In some examples, the light source produces a selectable wavelength, the return optical path includes one or more wavelength-selective elements, such as a filter or grating, and the system can perform spectroscopic measurements of the sample. In some examples, the sample can produce light wavelengths other than the incident wavelength(s), such as through fluorescence or Raman scattering; for these examples, the return path can also include a suitable wavelength-selective element.

The objective lens 104 can deliver incident light 106 from a light source 108 to the sample 102 through an annular illumination region of the pupil. In some examples, the annular illumination region extends fully around a central axis of the objective lens. In other examples, the annular illumination region extends partially around a central axis of the objective lens. In still other examples, the annular illumination region includes a plurality of non-contiguous subregions, the subregions all being equidistant from the central axis of the objective lens. In some examples, the annular illumination region can be defined by the light source, such as 108, having an annular shape. In some examples, the annular illumination region can be defined by a light source, such as 108, having a plurality of light-producing elements, such as light-emitting diodes (LEDs) arranged in an annular or circular pattern. In some examples, the annular illumination region can be defined by an anamorphic collimating or focusing lens, such as an axicon, that collimates or focuses light from the light-producing element (s) in the light source 108. In some examples, the annular illumination region can be defined by a mask that receives light and blocks a portion of the received light, where the blocked light is absorbed, scattered, or directed out of a desired optical path by reflection or transmission. In these examples, light reflected or transmitted by the mask along the desired optical path can have an annular footprint. In some examples, the annular illumination region can be defined by a combination of two or more of the above examples.

The objective lens 104 can further collect scattered light 110 returning from the sample 102 to form collected light 112. Scattered light 110 can propagate in any direction from a scattering location at or below a surface of the sample 102. Collected light 112 includes only the scattered light 110 that returns through the objective lens 104.

Confocal optics 114 can be positioned to receive the collected light 112. A detector 116 can be configured with the confocal optics 114 so that the detector 116 generates signals from light received from a specified depth 118 at or below a surface 120 of the sample 102 and rejects signals from light received from depths away from the specified depth 118. In some examples, the specified depth 118 can be selected so that a total optical path length traversed within the sample can equal, or can be relatively close to, an inverse of an expected scattering coefficient of the sample; the Appendix discusses this in detail. There are many possible configurations for confocal optics 114.

In some configurations, such as in the example of FIG. 1, the confocal optics physically block light arising from reflection and/or scattering at depths away from the specified depth. In the example of FIG. 1, confocal optics 114 are arranged in a pinhole configuration, where light originating at specified depth 118 is imaged onto a suitably sized pinhole 122 in a screen 124, transmits through the pinhole 122, and is detected by detector 116. Light originating at depths away from the specified depth 118 appears out-of-focus at the screen 124. The size of the out-of-focus light at the screen 124 is significantly larger than the pinhole 122, and the fraction of light transmitted through the pinhole 122 can be relatively small. In this manner, the pinhole configuration can retain only light originating from reflection and/or scattering at specified depth 118, and can extinguish or attenuate light originating from other depths. In some configurations, a portion of the confocal optics can be disposed in the incident optical path, in addition to the portion in the return optical path.

In other configurations, the light from other depths reaches the detector, and the system electronically filters out the contributions from the other depths. For instance, the confocal optics can include one or more modulating elements, such as one or more arrays of micromirrors or one or more arrays of acousto-optic modulators or electro-optic modulators. Incident light in the incident optical path and/or return light in the return optical path can strike the modulating elements, which can be configured to modulate different lateral portions of the incident and/or reflected light at unique assigned frequencies. By modulating the incident and/or return light twice, simultaneously, at the same unique assigned frequencies and at two different longitudinal locations between the light source 108 and the detector 116, inclusive, these configurations can simultaneously measure multiple lateral locations at specified depth 118, which can be advantageous over a pinhole configuration that only measures one location at a time.

In some examples, detector 116 can be a single-pixel detector, which produces an electrical signal in response to light incident thereon. In other examples, detector 116 can be a multi-pixel detector, with each pixel or group of pixels producing a respective electrical signal in response to light incident thereon. In some of these examples, the pixels can be arranged in a rectangular pattern. In other of these examples, the pixels can be irregularly shaped and/or irregularly positioned.

Detector 116 can provide one or more electrical signals to computer 126. In some examples, the computer 126 can receive at least one electrical signal from the detector, and can determine a physical property of the sample 102 based on the at least one electrical signal. In some examples, the detector 116 produces a first electrical signal in response to light at a first wavelength directed thereon. In these examples, the detector 116 produces a second electrical signal in response to light at the second wavelength directed thereon. In these examples, the computer 126 can be configured to produce a single measurement of a physical property of the sample in response to at least the first and second electrical signals.

For instance, computer 126 can perform a spectroscopic calculation to determine a concentration value of a particular substance within the sample. For these calculations, one or more ratios of measured reflectivity and/or scattering from the sample at two or more specified wavelengths can be compared with a lookup table of values. The computer 126 can determine a value of substance concentration within the sample from the lookup table, and can return the substance concentration as a single measurement of a physical property of the sample. The concentration is but one example, the confocal inspection system 100 can measure other suitable physical properties, such as refractive index, absorption, presence of a particular substance, scattering, scattering anisotropy and others.

Computer 126 can be included in a computer system that includes hardware, firmware and software. Examples may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media. In some examples, computer systems can include one or more processors, optionally connected to a network, and may be configured with instructions stored on a computer-readable storage device.

A mask 128 can be positioned between the objective lens 104 and the detector 116. The mask 128 can block portions of the collected light 112 located outside an annular collection region of the pupil. The mask 128 can define the annular collection region to be non-overlapping with the annular illumination region in the pupil. In some examples, the mask 128 can be positioned at an internal image of the pupil. In some examples, the mask 128 can be positioned on a beamsplitter 134. For some of these examples, the beamsplitter 134 can transmit incident light 106 from the light source 108 to the objective lens 104, and can reflect collected light 112 from the objective lens 108 to the confocal optics 114. For these examples, the mask 128 can include an opaque, diffuse, or non-reflective portion shaped to receive light outside the annular collection region of the pupil and absorb, scatter, or otherwise redirect the received light away from a desired optical path through the confocal optics 114. The mask can include a reflective portion (or a transmissive portion if the beamsplitter 134 is reflective) shaped to receive light inside the annular collection region of the pupil and direct the received light into a desired optical path through the confocal optics 114. In these examples, the border between these two mask portions can define a footprint of the light directed to the confocal optics 114, which can therefore define the annular collection region. In alternate configurations, the beamsplitter 134 can reflect incident light 106 and transmit the collected light 112. In these alternate configurations, the mask 128 can include an opaque, diffuse, or reflective portion to direct light away from the confocal optics, and a transmissive portion to direct light toward the confocal optics 114.

In some examples, the configuration of FIG. 1 can include one or more optional relay lenses, which can be located at suitable locations between the light source 108 and the beamsplitter 134, between the beamsplitter 134 and the confocal optics 114, and/or between the confocal optics 114 and the detector 116. Relay lenses can be used to form an internal image of one particular plane onto another plane. For instance, a relay lens can form an image of the objective lens pupil onto the beamsplitter 134, so that the mask 128 can be coincident with an image of the pupil. At this internal image of the pupil, the mask 128 can define the footprint of the transmitted or reflected light to be shaped as an annulus, a portion of an annulus, or more than one non-contiguous portion of an annulus. As another example, a relay lens can form an image of the objective lens pupil onto the detector 116. In some examples, an internal image of the pupil can be formed in the return optical path without using a relay lens. For instance, one or more lenses in the confocal optics can form an internal image of the pupil.

In the example of FIG. 1, the mask 128 is positioned on the beamsplitter 134. In other examples, the mask can be positioned at other locations in a return optical path between the objective lens 104 and the detector 116.

Figure 2:
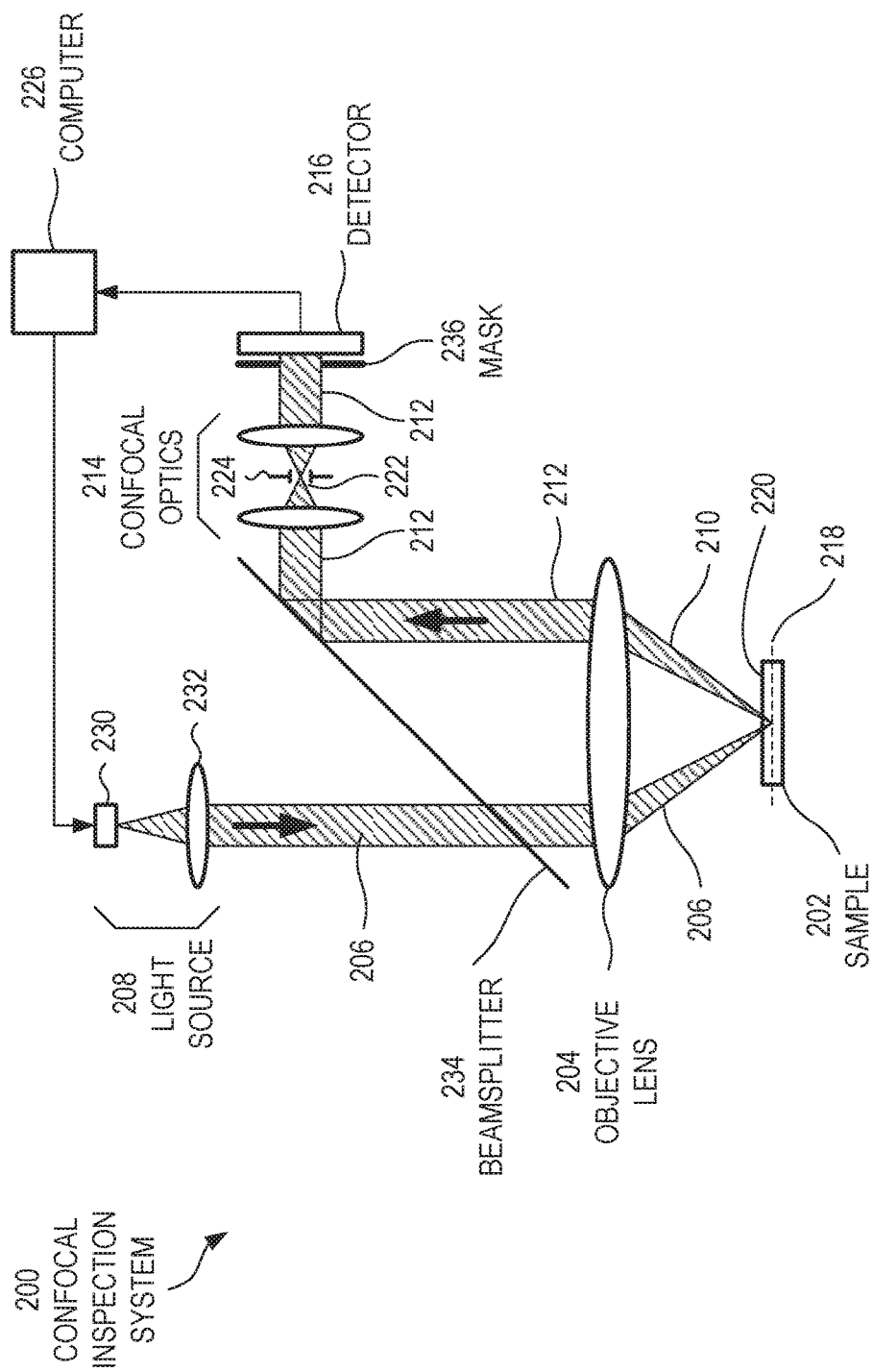
FIG. 2 is a schematic side view of another example of a confocal inspection system, in which the annular collection region is defined by a mask positioned between the confocal optics and the detector, in accordance with some embodiments.

FIG. 2 is a schematic side view of another example of a confocal inspection system 200, in which the annular collection region is defined by a mask 236 positioned between the confocal optics 214 and the detector 216, in accordance with some embodiments. Elements 202-234 in FIG. 2 are identical in structure and function to corresponding elements 102-134 in FIG. 1. Other positions for the mask can also be used. In some examples, the mask can be positioned on another element, such as a beamsplitter or a detector. In other examples, the mask can be configured as a stand-alone screen. In some examples, the mask can be positioned at an internal image of the pupil of the objective lens. In some of these examples, an optional relay lens can form an image of the pupil of the objective lens on the mask. In some of these examples, the mask can be shaped to define a footprint of a transmitted or reflected beam to have an annular shape, or a shape formed of a plurality of non-contiguous sections that fall along an annulus.

In the examples of FIGS. 1 and 2, the masks do not change their size or shape over time. In other examples, the elements that define the annular collection regions can be reconfigurable in time. For instance, FIG. 3 shows a system configuration in which the annular collection region is defined by a reconfigurable panel.

Figure 3:
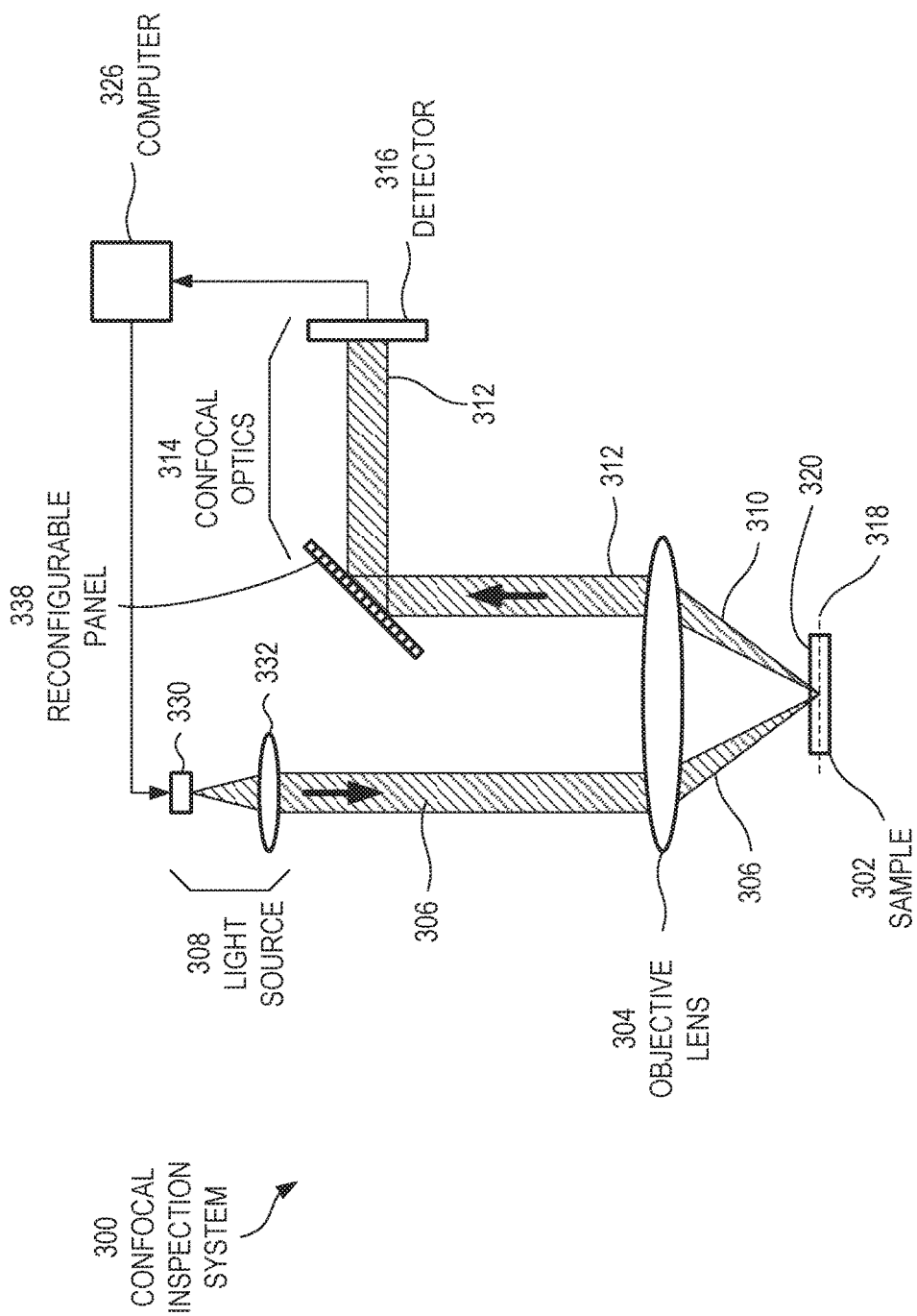
FIG. 3 is a schematic side view of another example of a confocal inspection system, in which the annular collection region is defined by a reconfigurable panel positioned between the objective lens and the detector, in accordance with some embodiments.

FIG. 3 is a schematic side view of another example of a confocal inspection system 300, in which the annular collection region is defined by a reconfigurable panel 338 positioned between the objective lens 304 and the detector 316, in accordance with some embodiments. Elements 302-332 in FIG. 3 are identical in structure and function to corresponding elements 202-232 in FIG. 2. The configuration of FIG. 3 is but one example of a confocal inspection system; other suitable configurations can also be used.

The confocal inspection system 300 can include an objective lens 304 having a pupil. The objective lens 304 can deliver incident light 306 to the sample 302 through an annular illumination region of the pupil. The objective lens 304 can further collect reflected or scattered light 310 returning from the sample 302 to form collected light 312. Confocal optics 314 can be positioned to receive the collected light 312. A detector 316 can be configured with the confocal optics 314 so that the detector 316 generates signals from light received from a specified depth 318 at or below a surface 320 of the sample 302 and rejects signals from light received from depths away from the specified depth 318.

The confocal inspection system 300 can include a reconfigurable panel 338 positioned between the objective lens 304 and the detector 316. In some examples, the reconfigurable panel 338 is positioned at an internal image of the pupil. The reconfigurable panel 338 can direct toward the detector 316 at least one portion of the collected light 312 located within an annular collection region of the pupil. The reconfigurable panel 338 can define the annular collection region to be non-overlapping with the annular illumination region in the pupil.

In some examples, the reconfigurable panel 338 can be an array of micromirrors. In other examples, the reconfigurable panel 338 can be an array of acousto-optic modulators, an array of electro-optic modulators, a pixelated liquid crystal panel sandwiched between two polarizers, multiple instances of any of the above, or other suitable reconfigurable elements.

In some examples, the reconfigurable panel 338 can be included in the confocal optics 314. For instance, in the example of FIG. 3, light from depths other than the specified depth 318 reaches the detector 316, and the system 300 electronically filters out the contributions from the other depths. For instance, the confocal optics 314 can include one or more modulating elements. Incident light in the incident optical path and/or return light in the return optical path can strike the modulating elements, which can be configured to modulate different lateral portions of the incident and/or reflected light at unique assigned frequencies. By modulating the incident and/or return light twice, simultaneously, at the same unique assigned frequencies and at two different longitudinal locations between the light source 308 and the detector 316, inclusive, these configurations can simultaneously measure multiple lateral locations at specified depth 318, which can be advantageous over a pinhole configuration that only measures one location at a time. One of the modulations can optionally be performed at the light source 308, which can switch on and off various light-producing elements 330 at unique assigned frequencies. One of the modulations can optionally be performed at the detector 316, which can produce one or more electrical signals having various frequencies that can be spectrally analyzed by the computer 326. In some examples, a beamsplitter can direct the incident light 306 onto the reconfigurable panel 338, so that the reconfigurable panel can modulate both the incident light 306 and the collected light 312.

In the examples of FIGS. 1-3, the systems include one or more elements that define the annular collection region in the return optical path before light in the return optical path strikes the detector. In other examples, the detector itself can define the annular collection region. For instance, FIG. 4 shows a system configuration in which the annular collection region is defined by the detector.

Figure 4:
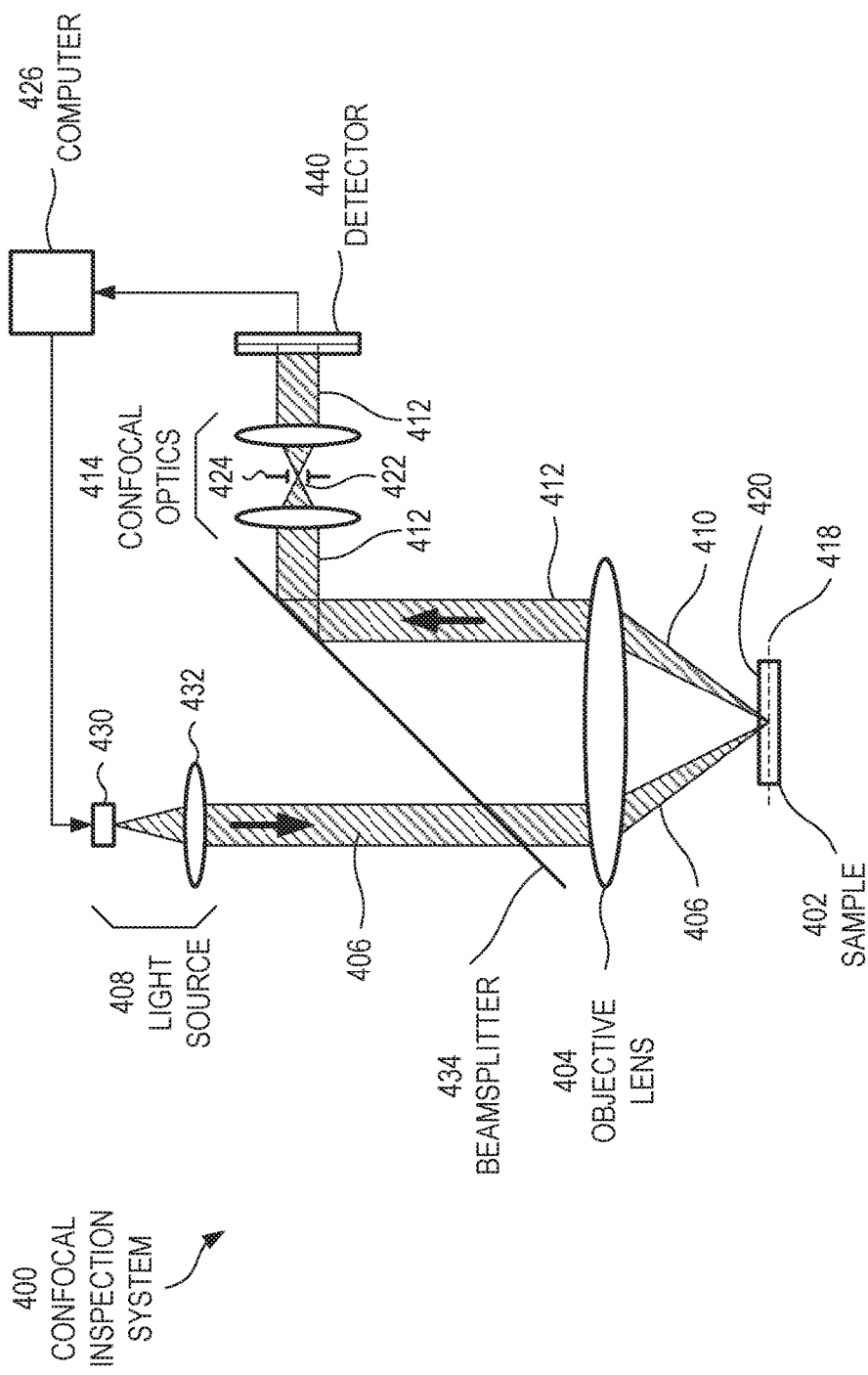
FIG. 4 is a schematic side view of another example of a confocal inspection system, in which the annular collection region is defined in hardware by the detector, in accordance with some embodiments.

FIG. 4 is a schematic side view of another example of a confocal inspection system 400, in which the annular collection region is defined in hardware by the detector 440, in accordance with some embodiments. Elements 402-434 in FIG. 3 are identical in structure and function to corresponding elements 302-334 in FIG. 3. The configuration of FIG. 4 is but one example of a confocal inspection system; other suitable configurations can also be used.

The confocal inspection system 400 can include an objective lens 404 having a pupil. The objective lens 404 can deliver incident light 406 to the sample 402 through an annular illumination region of the pupil. The objective lens 404 can further collect reflected or scattered light 410 returning from the sample 402 to form collected light 412. Confocal optics 414 can be positioned to receive the collected light 412. A detector 440 can be configured with the confocal optics 414 so that the detector 416 generates signals from light received from a specified depth 418 at or below a surface 420 of the sample 402 and rejects signals from light received from depths away from the specified depth 418.

The detector 440 can include a sensing area shaped to detect at least one portion of the collected light located within an annular collection region of the pupil. For instance, the sensing area can be shaped like a complete annulus, a portion of an annulus, or a plurality of non-contiguous portions of an annulus. In some examples, each portion from the sensing area can produce its own electrical signal. In other examples, the portions of the sensing area can be grouped to produce one or more electrical signals. The detector 440 can define the annular collection region to be non-overlapping with the annular illumination region in the pupil. In some examples, the detector 440 can be positioned at an internal image of the pupil.

In the example of FIG. 4, the annular collection region is defined in hardware. Specifically, in the example of FIG. 4, the shape of one or more elements of a sensing area defines the annular collection region. In other examples, the annular collection region can be defined in software. For example, FIG. 5 shows a system configuration in which the detector can be a multi-pixel detector, the computer can receive electrical signals from the multi-pixel detector, and the computer can define the annular collection region in software, rather than in hardware, as in FIG. 4.

Figure 5:
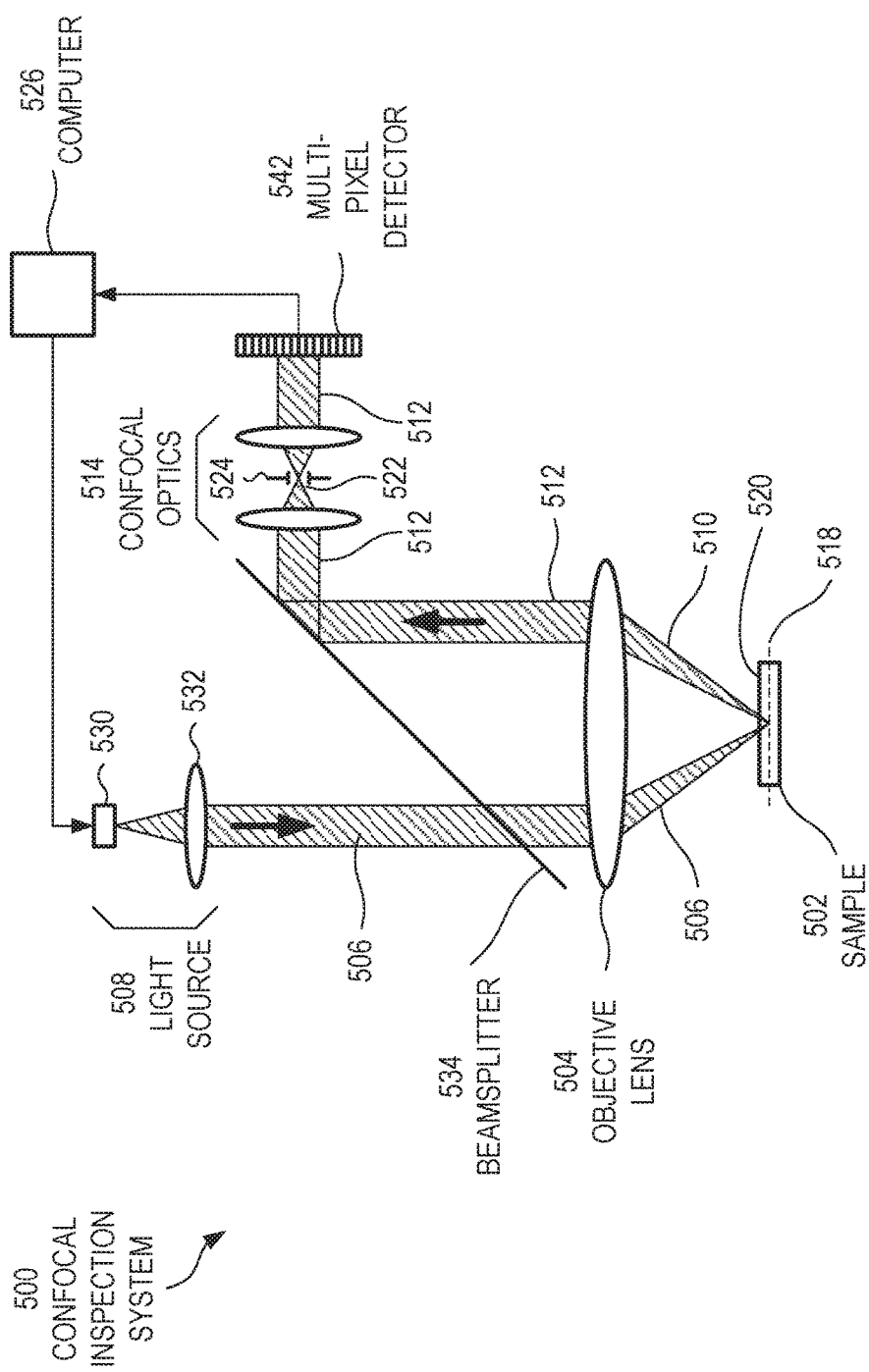
FIG. 5 is a schematic side view of another example of a confocal inspection system, in which the annular collection region is defined in software by the computer, in accordance with some embodiments.

FIG. 5 is a schematic side view of another example of a confocal inspection system 500, in which the annular collection region is defined in software by the computer 526, in accordance with some embodiments. Elements 502-534 in FIG. 3 are identical in structure and function to corresponding elements 402-434 in FIG. 4. The configuration of FIG. 5 is but one example of a confocal inspection system; other suitable configurations can also be used.

The confocal inspection system 500 can include an objective lens 504 having a pupil. The objective lens 504 can deliver incident light 506 to the sample 502 through an annular illumination region of the pupil. The objective lens 504 can further collect reflected or scattered light 510 returning from the sample 502 to form collected light 512. Confocal optics 514 can be positioned to receive the collected light 512.

A multi-pixel detector 542 can be configured with the confocal optics 514 so that the multi-pixel detector 542 generates signals from light received from a specified depth 518 at or below a surface 520 of the sample 502 and rejects signals from light received from depths away from the specified depth 518. The multi-pixel detector 542 can be positioned at an internal image of the pupil.

A computer 526 can receive a plurality of electrical signals from the multi-pixel detector 542. The computer 526 can identify a first subset of pixels of the multi-pixel detector 542. The first subset of pixels can have an outer boundary shaped to define the annular collection region to be non-overlapping with the annular illumination region in the pupil. The computer 526 can identify a first subset of the received electrical signals corresponding to the first subset of pixels. The computer 526 can average the first subset of the received electrical signals to form an averaged signal. The computer 526 can determine a physical property of the sample 502 based on the averaged signal.

In the examples of FIGS. 1-5, the systems use an objective lens having a single pupil. In any or all of these examples, the objective lens can be replaced with separate optics for illumination and collection.

Figure 6:
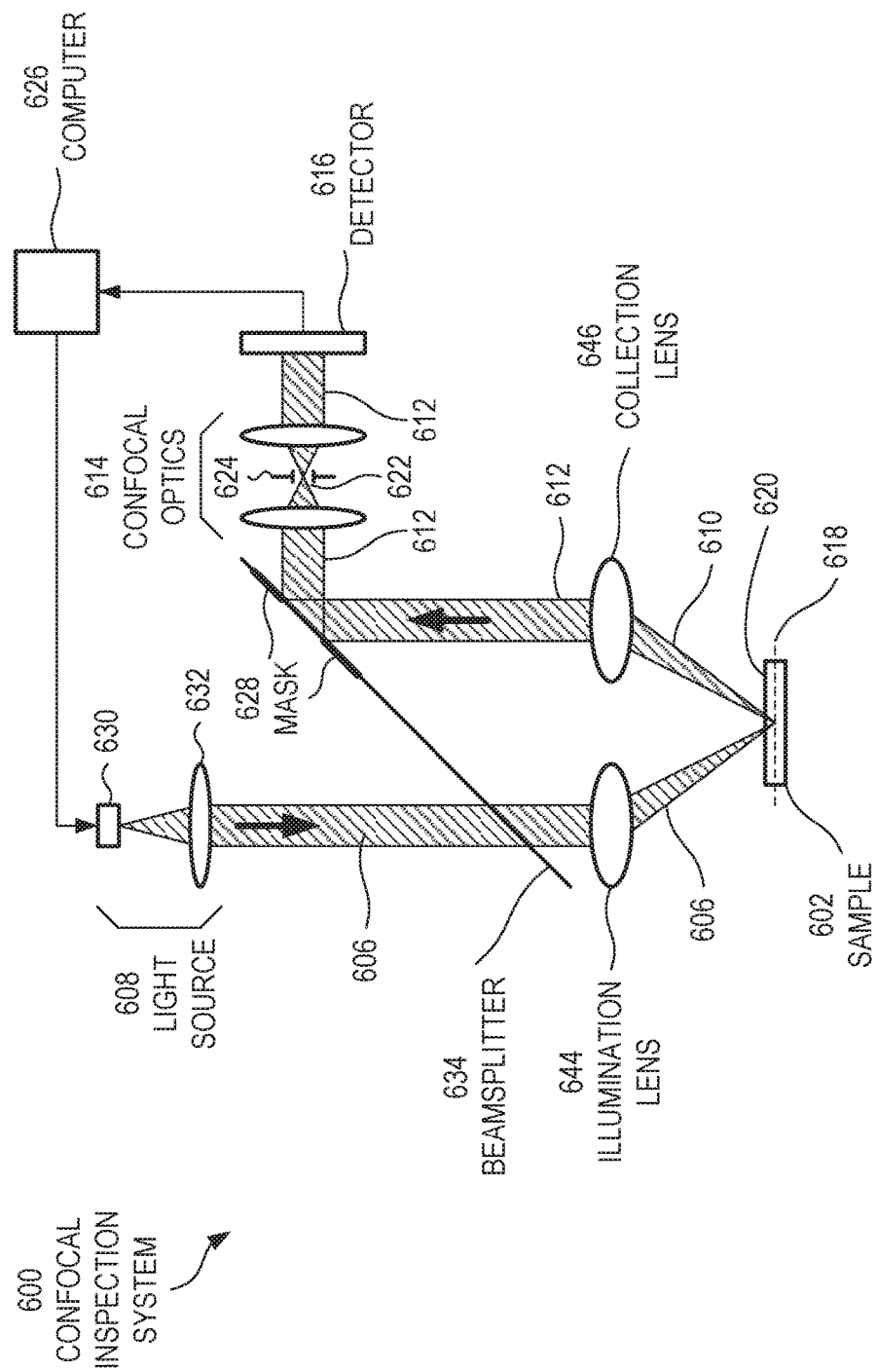
FIG. 6 is a schematic side view of another example of a confocal inspection system, having separate illumination and collection lenses, in accordance with some embodiments.

FIG. 6 is a schematic side view of another example of a confocal inspection system, having separate illumination and collection lenses, in accordance with some embodiments. Elements 602-634 in FIG. 6 are identical in structure and function to corresponding elements 102-134 in FIG. 1. The configuration of FIG. 6 is but one example of a confocal inspection system; other suitable configurations can also be used.

An illumination lens 644 can deliver incident light 606 to the sample 602 through an illumination pupil. A collection lens 646, separate from the illumination lens 644, can collect reflected or scattered light 610 returning from the sample 602 through a collection pupil to form collected light 612. For the purposes of this document, the separate illumination and collection pupils can be treated as a single pupil. Configurations using separate illumination and collection elements are discussed below with reference to FIG. 15.

In some instances, using separate lenses can deliver and extract light at higher angles of incidence and exitance than a single objective lens. Using separate lenses can also allow for flexibility in sizing and positioning some of the optical elements. The illumination and collection lenses can have the same focal length or can have different focal lengths. The lens pupils can be located in the same longitudinal plane or in different longitudinal planes, where the longitudinal direction is perpendicular to the top surface of the sample.

Figure 7:
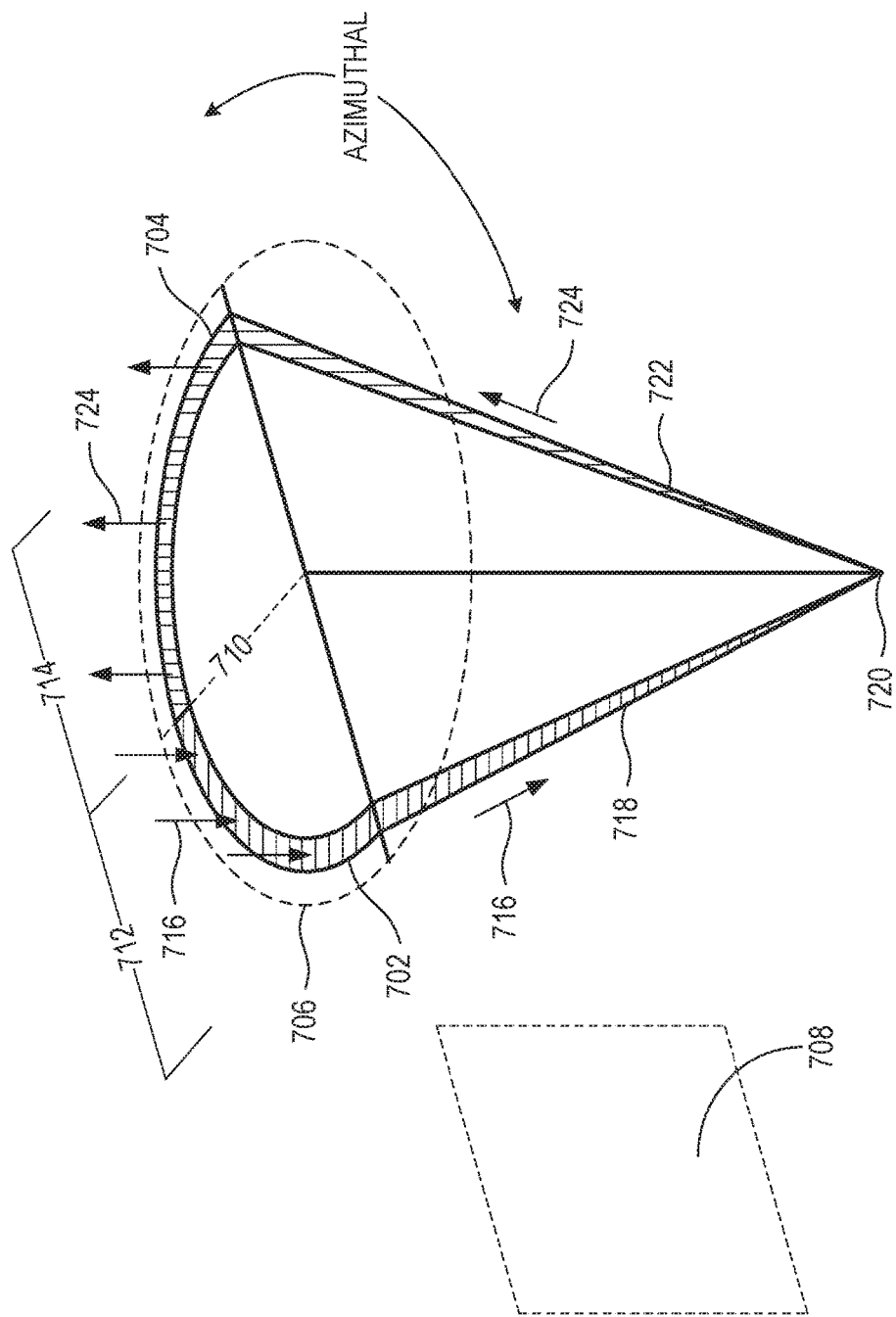
FIG. 7 shows a cross-section of an example of an annular illumination region and an annular collection region of an objective lens pupil, in accordance with some embodiments.

FIG. 7 shows a cross-section of an example of an annular illumination region 702 and an annular collection region 704 of an objective lens pupil 706, taken in a plane 708 perpendicular to both the objective lens pupil 706 and a line 710 separating the illumination (incident) portion 712 from the collection (return) portion 714, in accordance with some embodiments. Incident light 716 strikes objective lens pupil 706 in the region of incident annulus 702, and focuses as a converging cone 718 to a location 720 at or near the surface of a sample. The incident light 716 can reflect and/or scatter into many directions, with reflections and/or scattering originating from many depths within the sample, depending on the properties of the sample, but not all of the reflected and/or scattered light is detected by the optical system. Light rays that are detected are constrained to reside within diverging cone 722; all other rays are either blocked optically by the geometry of the annuli and the confocal optics, or are excluded electronically from the electrical signal or signals produced by the detector. The detected rays emerge from annular collection region 704 as collected light 724.

For many of the annular configurations described below, the annular illumination region and the annular collection region are said to be azimuthally distinct. For the purposes of this document, azimuthally distinct regions can be arranged to fall completely on opposite sides of a dividing line drawn through the center of the pupil. For example, wedges of a pie are said to be azimuthally distinct. In the geometry of FIG. 7, line 710 completely separates region 702 from region 704, so that regions 702 and 704 are azimuthally distinct.

FIGS. 8-14 are end-on views of examples of objective lens pupils having non-overlapping annular illumination regions and annular collection regions. These are merely examples; other configurations are also possible.

Figure 8:
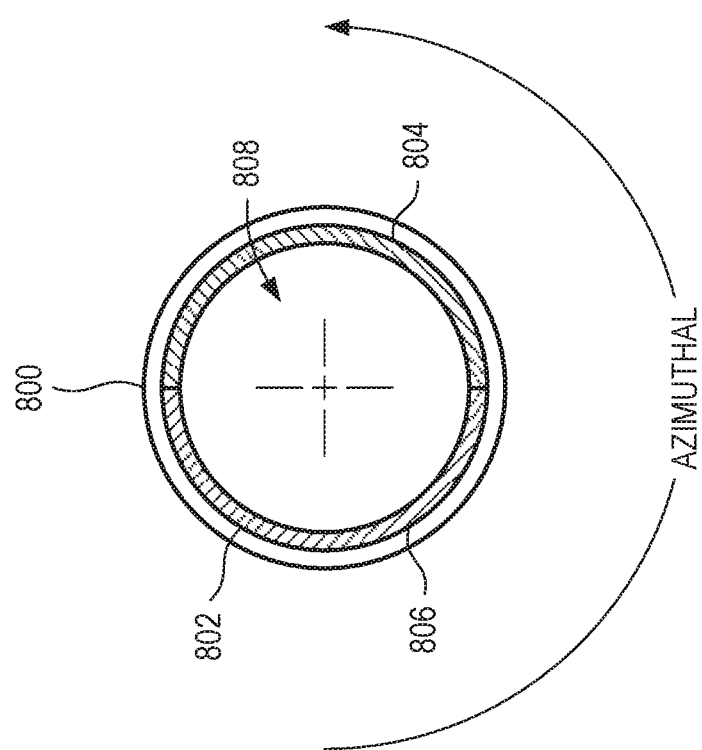
FIG. 8 is an end-on view of an example of an objective lens pupil, including an annular illumination region and an annular collection region formed as azimuthally distinct, complementary, non-overlapping halves of a single annulus, in accordance with some embodiments.

FIG. 8 is an end-on view of an example of an objective lens pupil 800, including an annular illumination region 802 and an annular collection region 804 formed as azimuthally distinct, complementary, non-overlapping halves of a single annulus 806, in accordance with some embodiments. A central portion 808 of objective lens pupil 800 is excluded from both annular illumination region 802 and annular collection region 804.

Figure 9:
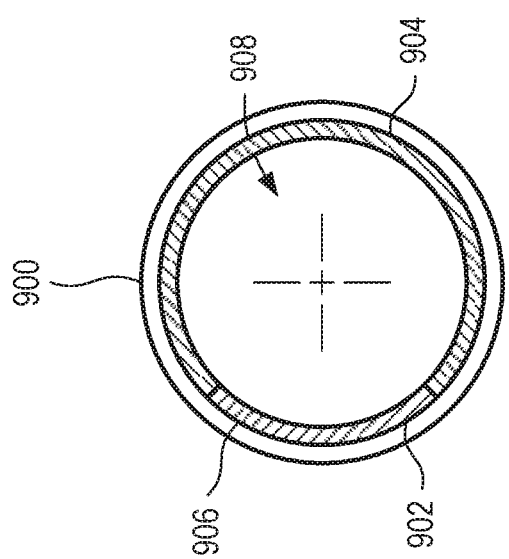
FIG. 9 is an end-on view of another example of an objective lens pupil, including an annular illumination region and an annular collection region formed as complementary and non-overlapping portions of a single annulus, in accordance with some embodiments.

FIG. 9 is an end-on view of another example of an objective lens pupil 900, including an annular illumination region 902 and an annular collection region 904 formed as complementary and non-overlapping portions of a single annulus 906, in accordance with some embodiments. Region 904 extends azimuthally more than halfway around the pupil 900. A central portion 908 of objective lens pupil 900 is excluded from both annular illumination region 902 and annular collection region 904.

Figure 10:
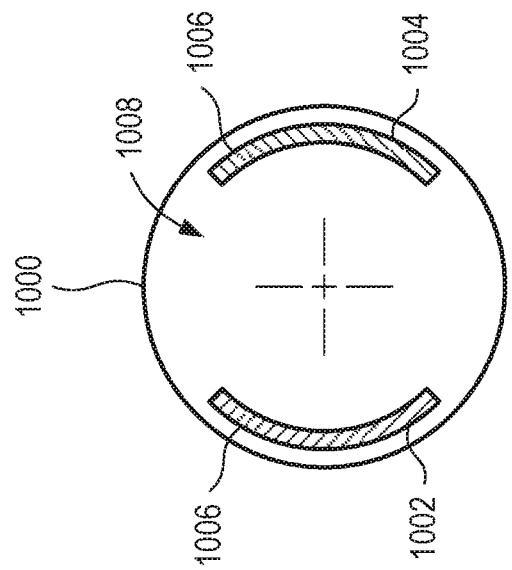
FIG. 10 is an end-on view of another example of an objective lens pupil, including an annular illumination region and an annular collection region formed as non-overlapping portions of a single annulus, in accordance with some embodiments.

FIG. 10 is an end-on view of another example of an objective lens pupil 1000, including an annular illumination region 1002 and an annular collection region 1004 formed as non-overlapping portions of a single annulus 1006, in accordance with some embodiments. Regions 1002 and 1004, taken together, do not extend azimuthally fully around the pupil 1000. A central portion 1008 of objective lens pupil 1000 is excluded from both annular illumination region 1002 and annular collection region 1004.

Figure 11:
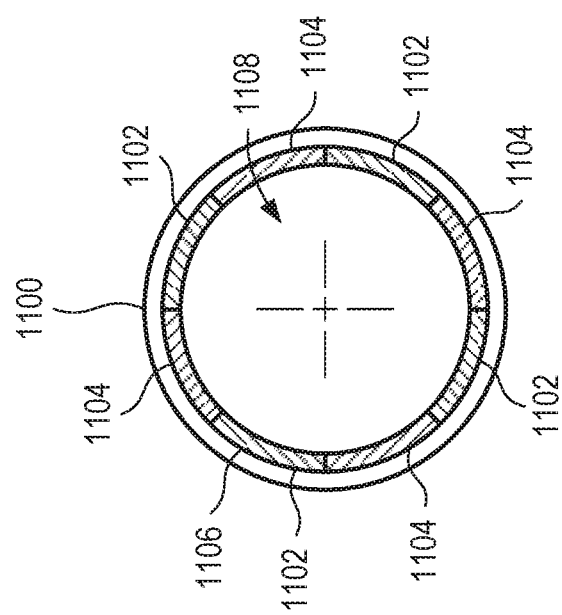
FIG. 11 is an end-on view of another example of an objective lens pupil, including an annular illumination region and an annular collection region, each formed as non-contiguous portions of a single annulus, in accordance with some embodiments.

FIG. 11 is an end-on view of another example of an objective lens pupil 1100, including an annular illumination region 1102 and an annular collection region 1104, each formed as non-contiguous portions of a single annulus 1106, in accordance with some embodiments. A central portion 1108 of objective lens pupil 1100 is excluded from both annular illumination region 1102 and annular collection region 1104.

Figure 12:
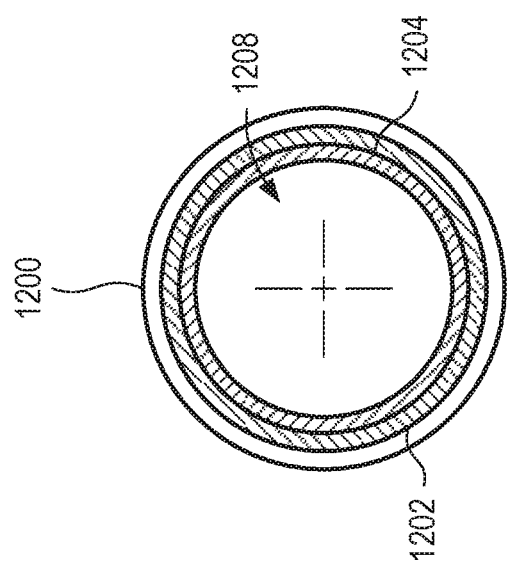
FIG. 12 is an end-on view of another example of an objective lens pupil, including an annular illumination region and an annular collection region, each formed as an azimuthally complete annulus, in accordance with some embodiments.

FIG. 12 is an end-on view of another example of an objective lens pupil 1200, including an annular illumination region 1202 and an annular collection region 1204, each formed as an azimuthally complete annulus, in accordance with some embodiments. Regions 1202 and 1204 are nested, concentric, and radially adjacent to each other. A central portion 12012 of objective lens pupil 1200 is excluded from both annular illumination region 1202 and annular collection region 1204.

Figure 13:
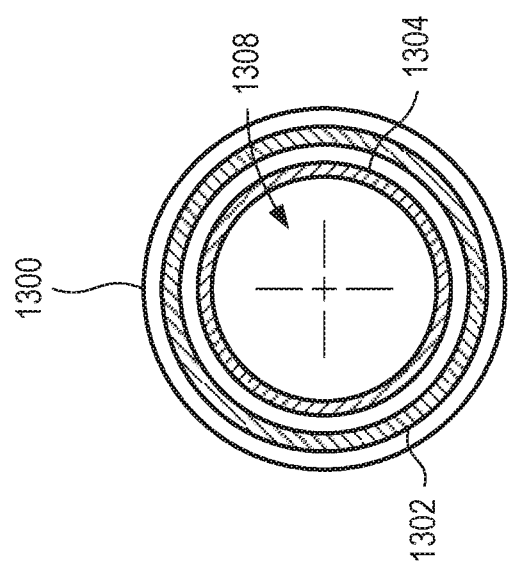
FIG. 13 is an end-on view of another example of an objective lens pupil, including an annular illumination region and an annular collection region, formed as azimuthally complete and spaced-apart annuli, in accordance with some embodiments.

FIG. 13 is an end-on view of another example of an objective lens pupil 1300, including an annular illumination region 1302 and an annular collection region 1304, formed as azimuthally complete and spaced-apart annuli, in accordance with some embodiments. Regions 1302 and 1304 are nested, concentric, and radially spaced apart from each other. A central portion 1308 of objective lens pupil 1300 is excluded from both annular illumination region 1302 and annular collection region 1304.

Figure 14:
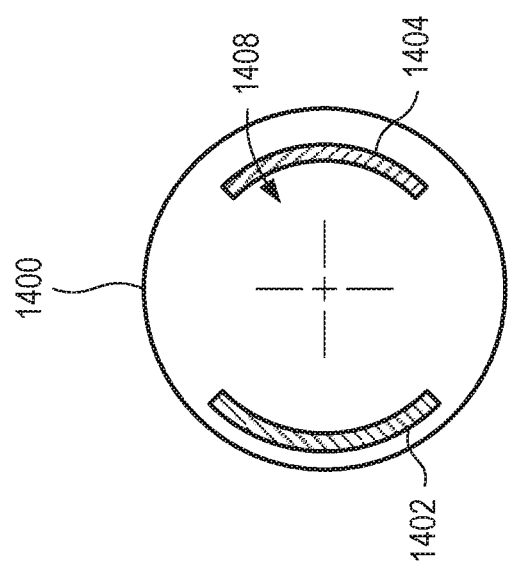
FIG. 14 is an end-on view of another example of an objective lens pupil, including an annular illumination region and an annular collection region, formed as azimuthally incomplete and spaced-apart annuli, in accordance with some embodiments.

FIG. 14 is an end-on view of another example of an objective lens pupil 1400, including an annular illumination region 1402 and an annular collection region 1404, formed as azimuthally incomplete and spaced-apart annuli, in accordance with some embodiments. A central portion 1408 of objective lens pupil 1400 is excluded from both annular illumination region 1402 and annular collection region 1404.

In all of the examples of FIGS. 8-14, a central portion of the pupil is excluded from both the annular illumination region and the annular collection region.

In all of the examples of FIGS. 8-14, both the annular illumination region and the annular collection region are concentric with a center of the pupil.

In the examples of FIGS. 8, 9, 11, and 12, the annular collection region and the annular illumination region, taken together, form a full annulus.

In the examples of FIGS. 8-11, the annular collection region and the annular illumination region are azimuthally distinct regions of a single annulus.

In the examples of FIGS. 12-14, the annular collection region and the annular illumination region are regions of different annuli.

In the examples of FIGS. 12 and 13, the annular collection region is an azimuthally complete annulus.

In the examples of FIGS. 9 and 13, the annular illumination region is an azimuthally complete annulus.

In the examples of FIGS. 12 and 13, the annular illumination region and the annular collection region comprise different, and azimuthally complete, annuli.

In the examples of FIGS. 8-10 and 12-14, at least one of the annular illumination region and the annular collection region includes a single, contiguous region.

In the example of FIG. 13, at least one of the annular illumination region and the annular collection region includes a plurality of non-contiguous regions.

Figure 15:
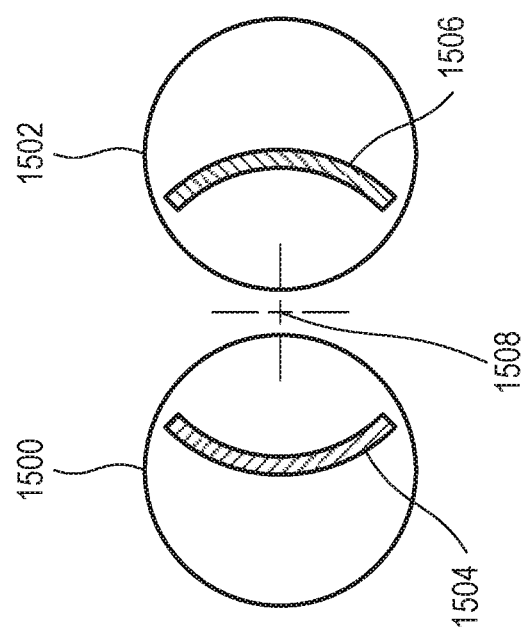
FIG. 15 is an end-on view of an example of pupils of the illumination and collection lenses, including an annular illumination region and an annular collection region formed in respective pupils of the illumination and collection lenses, in accordance with some embodiments.

FIG. 15 is an end-on view of an example of pupils 1500, 1502 of the illumination and collection lenses, including an annular illumination region 1504 and an annular collection region 1506 formed in respective pupils of the illumination and collection lenses, in accordance with some embodiments. In some examples, annular illumination region 1504 and annular collection region 1506 are concentric. In some examples, annular illumination region 1504 and annular collection region 1506 both exclude light directed to the sample or collected from the sample at normal incidence. In some examples, at least one of annular illumination region 1504 and annular collection region 1506 includes a single, contiguous region. In some examples, at least one of the annular illumination region and the annular collection region can include a plurality of non-contiguous regions.

Figure 16:
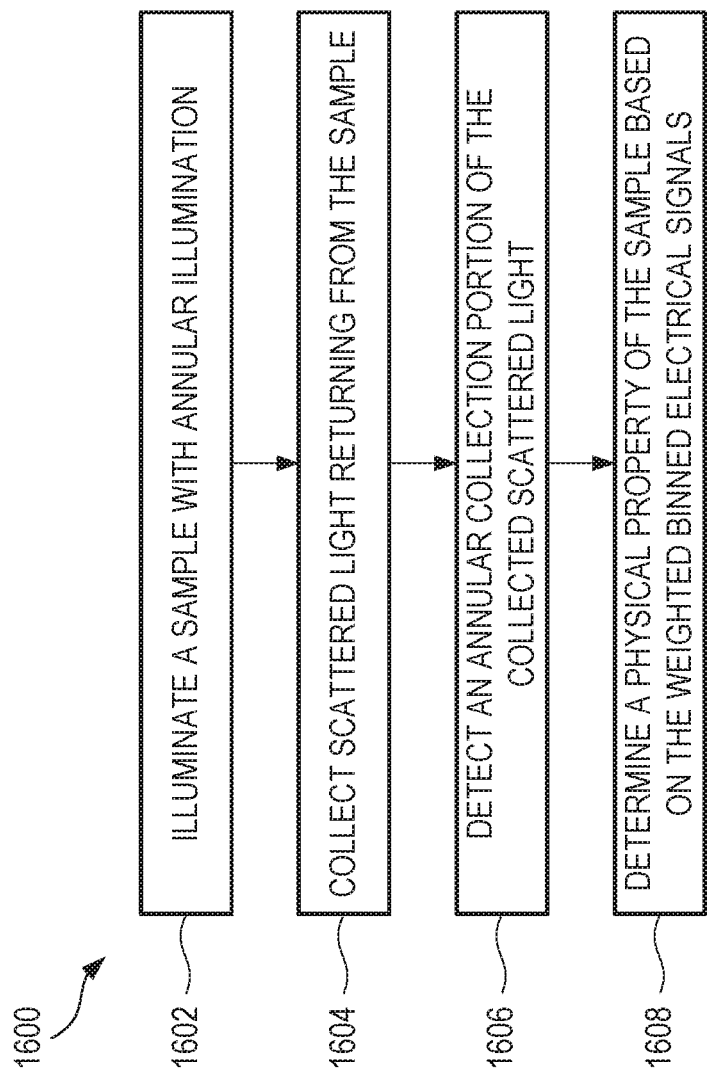
FIG. 16 is a flow chart of an example of a method of operation for optically characterizing a sample, in accordance with some embodiments.

FIG. 16 is a flow chart of an example of a method of operation 1600 for optically characterizing a sample, in accordance with some embodiments. The method 1600 can be executed by one or more of the confocal inspection systems shown in FIGS. 1-5, or by any suitable confocal inspection system. The method 1600 is but one example; other suitable methods of operation can also be used.

At 1602, method 1600 illuminates a sample with annular illumination. At 1604, method 1600 collects reflected or scattered light returning from the sample. At 1606, method 1600 detects an annular collection portion of the collected light. The annular collection portion can be non-overlapping with the annular illumination. At 1608, method 1600 determines a physical property of the sample based on the detected annular collection portion.

In some examples, method 1600 can further include blocking portions of the collected light located outside the annular collection region with a mask. In some examples, method 1600 can further include directing with a reconfigurable panel toward a detector at least one portion of the collected light located within the annular collection portion. In some examples, method 1600 can further include detecting the annular collection portion of the collected light with a detector, the detector including a sensing area shaped to detect at least one portion of the collected light located within the annular collection portion.

Using non-overlapping annular illumination and collection regions is but one technique for narrowing a range of optical path lengths traversed within the sample, which can be advantageous for absorptive or scattering samples. Other techniques are also possible.

Another technique for narrowing a range of optical path lengths traversed within the sample can use illumination and collection regions of the pupil, which, combined, have a surface area that is a fraction of the full pupil surface area (e.g., using angularly narrow illumination and collection). In this example, a confocal inspection system can optically characterize a sample. An objective lens, having a pupil, can deliver incident light from a light source through at least one illumination region of the pupil to the sample, and can collect light reflected or scattered from the sample through at least one collection region of the pupil. The illumination and collection regions are all non-overlapping in the pupil. In some examples, the illumination and collection regions, combined, have a surface area less than or equal to 50% of a surface area of the pupil. In some examples, the illumination and collection regions each have a surface area less than or equal to 10% of a surface area of the pupil. Confocal optics and a detector generate signals from light received from a specified depth at or below a surface of the sample and reject signals from light received from depths away from the specified depth.

Another technique for narrowing a range of optical path lengths traversed within the sample can use angularly narrow illumination and annular collection. In this example, a confocal inspection system can optically characterize a sample. An objective lens, having a pupil, can deliver incident light from a light source through an illumination region of the pupil to the sample. The incident light can have a reduced range of propagation angles at the sample. The objective lens can collect light from the sample through an annular collection region of the pupil. In alternate configurations, the incident and collected light can pass through separate incident and return lenses. Confocal optics can direct the collected light onto a detector, so that the detector generates signals from light received from a specified depth at or below a surface of the sample and rejects signals from light received from depths away from the specified depth. The angularly narrow incident light and annular collection region can narrow a range of optical path lengths traversed within the sample, which can be advantageous for absorptive or scattering samples.

Another technique for narrowing a range of optical path lengths traversed within the sample can use annular illumination and angularly narrow collection. In this example, a confocal inspection system can optically characterize a sample. An objective lens, having a pupil, can deliver incident light from a light source through an annular illumination region of the pupil to the sample. The objective lens can collect light from the sample through a collection region of the pupil. The collected light can have a reduced range of propagation angles leaving the sample. In alternate configurations, the incident and collected light can pass through separate incident and return lenses. Confocal optics can direct the collected light onto a detector, so that the detector generates signals from light received from a specified depth at or below a surface of the sample and rejects signals from light received from depths away from the specified depth. The annular incident light and angularly narrow collected light can narrow a range of optical path lengths traversed within the sample, which can be advantageous for absorptive or scattering samples.

For structured or inhomogeneous samples, it can be advantageous to average the incident and/or the return light. In this example, a confocal inspection system can optically characterize a sample. An objective lens, or separate incident and return lenses, can deliver incident light from a light source to the sample, and can collect light from the sample. Confocal optics can direct the collected light onto a detector. The system can average the incident light over multiple locations at the sample, for example, by scanning the incident light with a pivotable mirror in the incident and return optical paths, or by illuminating and collecting with multiple spaced-apart confocal apertures. The system can average the collected light, for example, by directing the collected light onto a single-pixel detector, or by directing the collected light onto a multi-pixel detector and averaging the pixel output signals to form a single electronic signal. Averaging the incident and/or return light can be advantageous for structured or inhomogeneous samples.

APPENDIX

The optical properties of a particular type of sample, such as human tissue, can vary from sample-to-sample, but often fall into a well-defined range of numerical values. For instance, a scattering coefficient of a particular sample typically falls within a particular range of scattering coefficients, where the range can represent a distribution of values of the scattering coefficient for a population of samples of the same type as the particular sample. The range can be centered around a so-called expected value, such as an expected scattering coefficient. In some examples, the expected values can be used when designing a geometry for an optical inspection system, with the expectation that most actual measured values will be relatively close to, but different from, the expected value.

In an optical inspection system designed to inspect a particular type of non-transparent sample, so that light propagating through the sample scatters and/or is absorbed by the sample as it propagates, the amount of scattering and/or absorption of the sample can influence the amount of light that reaches a detector in the optical inspection system. In other words, sample-to-sample variation of a scattering and/or absorption coefficient can produce a sample-to-sample variation in the optical power reaching a detector. Such sample-to-sample variation can be undesirable, and can underutilize a full dynamic range of the detector. It is possible to design the optical inspection system to have a decreased sensitivity of detected optical power to sample-to-sample variation in scattering coefficient.

An analytical model of the optical inspection system can assume that a light ray enters the sample at an input point, scatters a single time at a scattering location, changes direction just once at the scattering location, and exits the sample at an output point. In propagating from the input point to the scattering location, an input beam is attenuated by a factor $\exp[-A(\mu_s+\mu_a)]$, where quantities $\mu_s$ and $\mu_a$ are the scattering and absorption coefficients of the sample, respectively, and quantity A is an optical path length between the input point and the scattering location. At the scattering location, a fraction $\gamma\mu_s$ of the remaining input beam is scattered towards the output, where factor $\gamma$ accounts for a scattering phase function. The light scattered toward the output location is further attenuated by an amount $\exp[-B(\mu_s+\mu_a)]$ before exiting the sample, where quantity B is an optical path length between the scattering location and the output point. A fraction of optical power exiting the sample at the output location, divided by optical power entering the sample at the input location, is given by the quantity $\gamma\mu_s \exp[-L(\mu_s+\mu_a)]$, where quantity L equals quantity A+B, and is a total optical path length traversed within the sample.

The fraction of optical power exiting the sample is relatively insensitive when its derivative equals zero, e.g., when the total optical path length traversed within the sample, L, equals an inverse of the scattering coefficient of the sample, $1/\mu_s$. When $L=1/\mu_s$, the optical power reaching the detector is maximized, which is beneficial, and is relatively insensitive to sample-to-sample variations in the amount of scattering, which is also beneficial.

To take advantage of this relative insensitivity, the optical inspection system can be designed so that a total optical path length traversed within the sample can equal, or can be relatively close to, an inverse of an expected scattering coefficient of the sample. For instance, the total optical path length traversed within the sample can be within 0.1%, within 1%, within 10%, or within 50% of an inverse of an expected scattering coefficient of the sample. Other suitable values can also be used. The expected scattering coefficient can represent a distribution of values of the scattering coefficient for a population of samples of the same type as the particular sample, such as human tissue.

The above analysis assumes a single scattering event within the sample. For geometries in which a detector element receives light that is largely due to a single high-angle scattering event, the above analysis also holds for multiple scattering events and finite positional and angular resolutions. The above analysis can also apply to confocal detection with a narrow collimated input and angularly-constrained output.

The above Detailed Description and Appendix are intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The invention claimed is:

1. An optical inspection system for optically characterizing a sample, comprising:
    an objective lens having an annular illumination region and an annular collection region, wherein the annular illumination region and the annular collection region are non-overlapping, the objective lens configured to:
        deliver incident light to the sample through the annular illumination region, and
        collect reflected or scattered light returning from the sample through the annular collection region to form collected light;
    confocal optics positioned to receive the collected light;
    a detector configured with the confocal optics so that the detector generates signals from light received from a specified depth at or below a surface of the sample and rejects signals from light received from depths away from the specified depth; and
    a mask positioned between the objective lens and the detector, the mask blocking non-annular portions of the collected light.

2. The optical inspection system of claim 1, further comprising a beamsplitter disposed between the objective lens and the confocal optics, wherein the mask is disposed on the beamsplitter.

3. The optical inspection system of claim 1, wherein the mask is positioned between the confocal optics and the detector.

4. The optical inspection system of claim 1, further comprising a computer configured to:
    receive at least one electrical signal from the detector; and
    determine a physical property of the sample based on the at least one electrical signal.

5. A method for optically characterizing a sample, comprising:
    illuminating a sample through an annular illumination region of an objective lens;
    collecting reflected or scattered light returning from the sample through an annular collection region of the objective lens, wherein the annular illumination region and the annular collection region of the objective lens are non-overlapping;
    blocking non-annular portions of the collected reflected or scattered light using a mask;
    detecting an annular collection portion of the collected light; and
    determining a physical property of the sample based on the detected annular collection portion.

6. The method of claim 5, further comprising:
    blocking portions of the collected light located outside the annular collection region with a mask.

7. The method of claim 5, further comprising:
    directing with a reconfigurable panel toward a detector at least one portion of the collected light located within the annular collection portion.

8. The method of claim 5, further comprising:
    detecting the annular collection portion of the collected light with a detector, the detector including a sensing area shaped to detect at least one portion of the collected light located within the annular collection portion.

* * * * *